United States Patent [19]

Meyer et al.

[11] Patent Number: 4,885,303

[45] Date of Patent: Dec. 5, 1989

[54] CIRCULATION-ACTIVE TETRAHYDROPYRIDINE-3-CARBONITRILE DERIVATIVES

[75] Inventors: Horst Meyer, West Haven, Conn.; Eckhard Schwenner, Wuppertal; Andreas Knorr, Erkrath, both of Fed. Rep. of Germany

[73] Assignee: Bayer Aktiengesellschaft, Leverkusen, Fed. Rep. of Germany

[21] Appl. No.: 141,363

[22] Filed: Jan. 4, 1988

[30] Foreign Application Priority Data

Jan. 8, 1987 [DE] Fed. Rep. of Germany ....... 3700307

[51] Int. Cl.$^4$ .................. C07D 213/55; C07D 213/57; A61K 31/44
[52] U.S. Cl. .................... 514/332; 514/336; 514/344; 546/263; 546/284; 546/286
[58] Field of Search ....... 546/286, 284, 263; 514/344, 336, 332

[56] References Cited

FOREIGN PATENT DOCUMENTS 0110073 6/1984 European Pat. Off. ............ 546/286
3414801 10/1985 Fed. Rep. of Germany ...... 546/286

OTHER PUBLICATIONS

Chemical Abstract, vol. 79, No. 15, Oct. 15, 1973, Columbus, Ohio, M. F. Chasle-Pommert et al., "Reactions of Travalent Phosphorus Compounds with Positive Halogen Compound", p. 418.

Primary Examiner—Alan L. Rotman
Attorney, Agent, or Firm—Sprung Horn Kramer & Woods

[57] ABSTRACT

Circulation active tetrahydropyridines of the formula

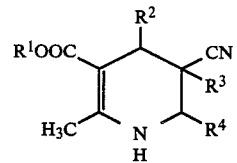

in which $R^1$ represents a straight-chain, branched or cyclic, saturated or unsaturated hydrocarbon radical which has up to 20 carbon atoms and can be interrupted in the chain by an oxygen atom or a sulphur atom and/or can be substituted by halogen, cyano, hydroxyl, acyloxy, nitro or nitrooxy, or by a phenyl, phenoxy, phenylthio or phenylsulphonyl group which is optionally substituted by halogen, cyano, dialkylamino with in each case 1 or 2 carbon atoms per alkyl group, alkoxy with 1 to 4 carbon atoms, alkyl with 1 to 4 carbon atoms, trifluoromethyl or nitro, or by an $\alpha$-, $\beta$- or $\gamma$-pyridyl group, or by an amino group, this amino group carrying 2 identical or different substituents from the group comprising alkyl with up to 4 carbon atoms, alkoxyalkyl with up to 4 carbon atoms, phenyl and aralkyl, and these substitutents optionally forming, with the nitrogen atom, a 5- to 7-membered ring which can contain, as a further hetero atom, an oxygen or sulphur atom or an N-phenyl or N-alkyl grouping, this alkyl group containing 1 to 3 carbon atoms, $R^2$ represents phenyl, naphthyl, thienyl, furyl, pyrryl, pyrazolyl, imidazolyl, oxazolyl, isoxazolyl, thiazolyl, pyridyl, pyridazinyl, pyrimidyl, pyrazinyl, indolyl, benzimidazolyl, benzoxazolyl, benzisoxazolyl, benzoxadiazolyl, benzothiadiazolyl, quinolyl, isoquinolyl, quinazolyl or quinoxalyl;

wherein m denotes a number from 0 to 2 and alkyl contains 1 to 4 carbon atoms with optionally 1 to 3 fluorine atoms, $R^3$ represents a group of the formula —CN or —COOR$^5$, wherein $R^5$ has the same meaning as $R^1$ and can be identical to or different from this radical, and $R^4$ represents hydrogen, or represents phenyl or naphthyl, and their pharmaceutically acceptable acid addition salts.

10 Claims, No Drawings

CIRCULATION-ACTIVE TETRAHYDROPYRIDINE-3-CARBONITRILE DERIVATIVES

The present invention relates to new tetrahydropyridine compounds, a process for their preparation and their use in medicaments, in particular in medicaments which influence the circulation.

The invention relates to tetrahydropyridine compounds of the general formula (I)

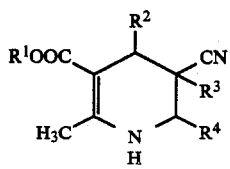

in which $R^1$ represents a straight-chain, branched or cyclic, saturated or unsaturated hydrocarbon radical which has up to 20 carbon atoms and can be interrupted in the chain by an oxygen atom or a sulphur atom and/or can be substituted by halogen, cyano, hydroxyl, acyloxy, nitro or nitrooxy, or by a phenyl, phenoxy, phenylthio or phenylsulfphonyl group which is optionally substituted by halogen, cyano, dialkylamino with in each case 1 or 2 carbon atoms per alkyl group, alkoxy with 1 or 4 carbon atoms, alkyl with 1 to 4 carbon atoms, trifluoromethyl or nitro, or by an $\alpha$-, $\beta$- or $\gamma$-pyridyl group, or by an amino group, this amino group carrying 2 identical or different substituents from the group comprising alkyl with up to 4 carbon atoms, alkoxyalkyl with up to 4 carbon atoms, phenyl and aralkyl, and these substituents optionally forming, with the nitrogen atom, a 5- to 7-membered ring which can contain, as a further hetero atom, an oxygen or sulphur atom or an N-phenyl or N-alkyl grouping, this alkyl group containing 1 to 3 carbon atoms, $R^2$ represents phenyl, naphthyl, thienyl, furyl, pyrryl, pyrazolyl, imidazolyl, oxazolyl, isoxazolyl, thiazolyl, pyridyl, pyridazinyl, pyrimidyl, pyrazinyl, indolyl, benzimidazolyl, benzoxazolyl, benzisoaxazolyl, benzoxadiazolyl, benzothiadiazolyl, quinolyl, isoquinolyl, quinazolyl or quinoxalyl, it being possible for the ring systems mentioned in each case to be substituted by 1 or 2 identical or different substituents from the group comprising phenyl, straight-chain or branched alkyl with 1 to 8 carbon atoms, cycloalkyl with 3 to 7 carbon atoms, alkoxy with 1 to 4 carbon atoms, trimethylene, tetramethylene, pentamethylene, dioxymethylene, dioxyethylene, halogen, trifluoromethyl, trifluoromethoxy, difluoromethoxy, tetrafluoroethoxy, nitro, cyano and $SO_m$-alkyl, wherein m denotes a number from 0 to 2 and alkyl preferably contains 1 to 4 carbon atoms with optionally 1 to 3 fluorine atoms, $R^3$ represents a group of the formula -CN or -COOR$^5$, wherein $R^5$ has the same meaning as $R^1$ and can be identical to or different from this radical, and $R^4$ represents hydrogen, or represents phenyl or naphthyl, it being possible for the ring systems mentioned to be substituted by up to 2 identical or different substituents from the series comprising nitro, cyano, alkyl with 1 to 4 carbon atoms, alkoxy with 1 to 4 carbon atoms, halogen, trifluoromethyl, trifluoromethoxy and trifluoromethylthio, and their pharmaceutically acceptable acid addition salts.

The compounds according to the invention exist in stereoisomeric forms which either behave as mirror images (enantiomers) or do not behave as mirror images (diastereomers). The invention relates both to the antipodes and to the racemic forms as well as to the diastereomer mixtures. Like the diastereomers, the racemic forms can be resolved into the stereoisomerically uniform constituents in a known manner (compare E.L. Eliel, Stereochemistry of Carbon Compounds, McGraw Hill, 1962).

Pharmaceutically acceptable salts can be salts of the compounds according to the invention with inorganic or organic acids. Preferred salts are those with inorganic acids, such as, for example, hydrochloric acid, hydrobromic acid, phosphoric acid or sulphuric acid, or salts of the compounds according to the invention with organic carboxylic acids or sulphonic acids, such as, for example, formic acid, acetic acid, propionic acid, maleic acid, fumaric acid, malic acid, citric acid, tartaric acid, lactic acid, malonic acid or benzoic acid, or methanesulphonic acid, ethanesulphonic acid, phenylsulphonic acid, toluenesulphonic acid or naphthalenedisulphonic acid.

Compounds which may be mentioned as preferred are those of the general formula (I) in which $R^1$ represents a straight-chain, branched or cyclic, saturated or unsaturated hydrocarbon radical which has up to 14 carbon atoms and can be interrupted in the chain by an oxygen atom and/or be substituted by fluorine, chlorine, bromine, iodine, cyano, hydroxyl, acetoxy or nitrooxy, or by a phenyl or phenoxy group which is optionally substituted by fluorine, chlorine, bromine, alkoxy with 1 to 4 carbon atoms, alkyl with 1 to 4 carbon atoms or trifluoromethyl, or by an a-, B- or y-pyridyl group, or by an amino group, this amino group carrying 2 identical or chlorine, bromine, alkoxy with 1 to 4 carbon atoms, alkyl with 1 to 4 carbon atoms or trifluoromethyl, or by an $\alpha$-, $\beta$- or $\gamma$-pyridyl group, or by an amino group, this amino group carrying 2 identical or different substituents from the group comprising alkyl with 1 to 4 carbon atoms, phenyl and benzyl, $R^2$ represents phenyl, naphthyl, thienyl, furyl, pyridyl, pyrimidyl, quinolyl or benzoxadizolyl, it being possible for the ring systems mentioned to be substituted by 1 or 2 identical or different substituents from the group comprising phenyl, alkyl with 1 to 4 carbon atoms, alkoxy with 1 or 2 carbon atoms, dioxymethylene, fluorine, chlorine, bromine, iodine, trifluoromethyl, trifluoromethoxy, difluoromethoxy, trifluoromethylsulphonyl, alkylthio with 1 to 4 carbon atoms, nitro and cyano, $R^3$ represents a group of the formula -CN or -COOR$^5$, wherein $R^5$ has the same meaning as $R^1$ and can be identical to or different from this radical, and $R^4$ represents hydrogen, or represents phenyl, which can be mono- or disubstituted by identical or different substituents from the group comprising nitro, cyano, methyl, methoxy, fluorine, chlorine, bromine, iodine, trifluoromethyl and trifluoromethoxy, and their pharmaceutically acceptable salts.

Compounds which may be mentioned as particularly preferred are those of the general formula (I) in which $R^1$ represents a straight-chain, branched or cyclic hydrocarbon radical which has up to 8 carbon atoms and can be interrupted in the chain by an oxygen atom and/or can be substituted by fluorine, cyano, acetoxy, hydroxyl, phenyl, phenoxy, or α-, β- or γ-pyridyl, or by an amino group, this amino group carrying two identical or different substituents from the group comprising alkyl with 1 or 2 carbon atoms and benzyl, $R^2$ represents phenyl, naphthyl, thienyl, pyridyl or benzoxadiazolyl, it being possible for the ring systems mentioned to be substituted by 1 or 2 identical or different substituents from the group comprising chlorine, trifluoromethyl, nitro and cyano, $R^3$ represents a group of the formula —CN or —COOR$^5$, wherein $R^5$ has the same meaning as $R^1$ and can be identical to or different from this radical, and $R^4$ represents hydrogen, or represents phenyl, which can be substituted by nitro, fluorine, chlorine or trifluoromethyl, and their pharmaceutically acceptable salts.

The compounds of the general formula (I) according to the invention are obtained by a process in which ylidene compounds of the general formula (II)

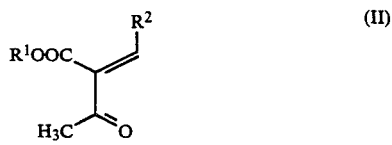

in which $R^1$ and $R^2$ have the abovementioned meaning, are reacted with cyanoethenes of the general formula (III)

in which $R^3$ and $R^4$ have the abovementioned meaning, in the presence of ammonia or a suitable ammonium salt in inert solvents.

If ethyl 2-trifluorobenzylideneacetoacetate, benzylidenemalodinitrile and ammonia are used as the starting substances, the process according to the invention can be illustrated by the following equation:

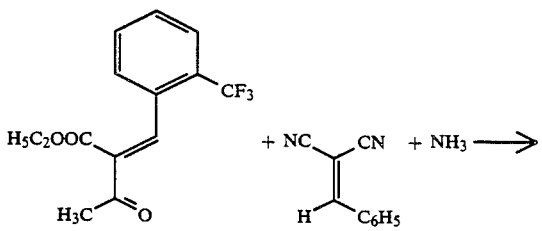

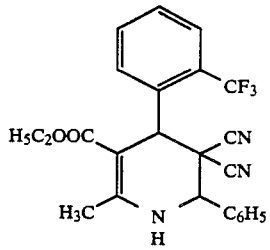

Suitable inert solvents are water or organic solvents which do not change under the reaction conditions. These include, preferably, alcohols, such as methanol, ethanol, propanol or isopropanol, or halogenohydrocarbons, such as methylene chloride, chloroform, carbon tetrachloride, 1,2-dichloroethane or dichloroethylene, or ethers, such as diethyl ether, dioxane or tetrahydrofuran, or hydrocarbons, such as benzene, toluene or xylene, or amides, such as dimethylformamide or hexamethylenephosphoric acid triamide, or ammonia or glacial acetic acid. It is also possible to use mixtures of the solvents mentioned.

The reaction is in general carried out in a temperature range from 0° C. to +200° C., preferably from +20° C. to +150° C.

The reaction can be carried out under normal pressure, under increased pressure or under reduced pressure. It is in general carried out under normal pressure.

The reaction is in general carried out by a procedure in which the ylidene compound and the cyanoethene are mixed in a suitable solvent with concentrated ammonia solution, if appropriate with a suitable ammonium salt, and if appropriate the mixture is heated. The reaction product is in general worked up by extraction, chromatography and/ or crystallization.

Suitable ammonium salts can be salts of ammonia with inorganic or organic acids. Examples which may be mentioned are: halides, such as chlorides or bromides, sulphates, hydrogen sulphates, hydrogen phosphates, carbonates, bicarbonates or acetates.

Ammonium acetate is particularly preferably employed. In this case, acetic acid is particularly preferably used as the solvent.

In carrying out the reaction, the ylidene compound is in general used in an amount of 1 to 5 mols, preferably 1 to 2.5 mols, per mol of the cyanoethene compounds. Ammonia or a suitable ammonium salt is in general used in an amount of 1 to 10, preferably 1 to 5 mols per mol of the xylidene compound.

The ylidene compounds used as starting substances are known or can be prepared by known methods [G. Jones "The Knoevenagel Condensation" in Organic Reaktions XV, 204 (1967)].

The cyanoethene compounds of the general formula (II) are known or can be prepared by known methods [Beilstein's Handbuch der organischen Chemie (Beilstein's Handbook of Organic Chemistry) 3 (1), 134; 9, 893].

The new compounds have a broad and diverse pharmacological action spectrum.

In detail, it has been possible to demonstrate the following main actions in animal experiments.

(1.) On parenteral, oral or perlingual administration, the compounds cause a clear and long-lasting dilation of the coronary vessels. This action on the coronary vessels is intensified by a simultaneous nitrite-like effect of relieving the load on the heart. They influence or modify cardiac metabolism in the sense of a saving in energy.

(2.) The excitability of the stimulus formation and excitation conduction system within the heart is reduced, so that an antifibrillation effect detectable in therapeutic doses results.

(3.) The tone of the smooth muscle of the vessels is greatly reduced under the action of the compounds. This vasospasmolytic action can take place in the entire vascular system or can manifest itself more or less isolated in circumscribed vacular regions.

(4.) The compounds reduce the blood pressure of normotensive and hypertensive animals and can therefore be used as antihypertensive agents.

(5.) The compounds have a potent musculospasmolytic action which manifests itself on the smooth muscle of the gastrointestinal tract, the urogenital tract and the respiratory system.

On the basis of these properties, the compounds according to the invention are particularly suitable for the prophylaxis and therapy of acute and chronic ischaemic heart diseases in the broadest sense, for the therapy of hypertension and for the treatment of disturbances in cerebral and peripheral circulation.

The new active compounds can be converted in a known manner into the customary formulations, such as tablets, dragees, pills, granules, aerosols, syrups, emulsions, suspensions and solution, using inert non-toxic pharmaceutically suitable excipients or solvents. The therapeutically active compound here should in each case be present in a concentration of about 0.5 to 90% by weight of the total mixture, that is to say in amounts which are sufficent to achieve the stated dosage range.

The formulations are prepared, for example, by extending the active compounds with solvents and/or excipients, if appropriate using emulsifying agents and/or dispersing agents, and, for example, in the case of the use of water as the diluent, organic solvents can be used as auxiliary solvents if appropriate.

Examples of auxiliaries which may be mentioned are: water, non-toxic organic solvents, such as paraffins (for example petroleum fractions), vegetable oils (for example groundnut/sesame oil), alcohols (for example ethyl alcohol and glycerol), carriers, such as, for example, natural rock powders (for example kaolins, aluminas, talc and chalk), synthetic rock powders (for example highly disperse silicic acid and silicates), sugars (for example sucrose, lactose and glucose), emulsifying agents (for example polyoxyethylene fatty acid esters and polyoxyethylene fatty alcohol ethers, alkyl sulphonates nd aryl sulphonates ), dispersion agents (for example lignin, sulphite waste liquors, methylcellulose, starch and polyvinylpyrrolidone) and lubricants (for example magnesium stearate, talc, stearic acid and sodium sulphate).

The administration is carried out in the customary manner, preferably orally or parenterally, in particular perlingually or intravenously. In the case of oral use, tablets can of course also contain, in addition to the excipients mentioned, additives such as sodium citrate, calcium carbonate and dicalcium phosphate, together with various additional substances, such as starch, preferably potato starch, gelatin and the like. Lubricants, such as magnesium stearate, sodium lauryl sulphate and talc, can furthermore be co-used for tablet-making. In the case of aqueous suspensions, various flavor-improving agents or colourants can be added to the active compounds, in addition to the abovementioned auxiliaries.

In the case of parenteral administration, solutions of the active compounds can be employed, using suitable liquid excipients.

In general, it has proved advantageous in the case of intravenous administration to administer amounts of about 0.001 to 1 mg/kg, preferably about 0.02 to 0.5 mg/kg of body weight to achieve effective results, and in the case of oral administration the dosage is about 0.01 to 20 mg/kg, preferably 0.1 to 10 mg/kg of body weight.

Nevertheless, it may at times be necessary to deviate from the amounts mentioned, and in particular to do so as a function of the body weight or the nature of the administration route, and of the individual behaviour towards the medicament, the nature of its formulation and the time or interval at which administration takes place. Thus, in some cases it can suffice to manage with less than the abovemention minimum amount, whilst in other cases the upper limit mentioned must be exceeded. Where relatively large amounts are administered, it may be advisable to divide these into several individual doses over the course of the day.

PREPARATION EXAMPLES

Example 1
Diethyl 3-cyano-6-methyl-2,4-diphenyl-1,2,3,4-tetrahydroopyridine-3,5-dicarboxylate

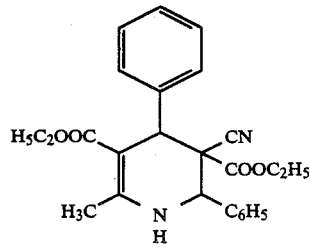

A mixture of 11.0 g (0.5 mol) of ethyl benzylideneacetoacetate, 10.0 g (0.05 mol) of ethyl α-cyanocinnamate, 50 ml of ethanol and 5.5 ml of concentrated ammonia solution is stirred at room temperature for 1 day. After evaporation, the residue is recrystallized from isopropanol.
Yield: 10.5 g
Melting point: 142° C.

Example 2
Deithyl 3-cyano-6-methyl-4-(3-nitrophenyl)-1,2,3,4-tetrahydropyridine-3,5-dicarboxylate

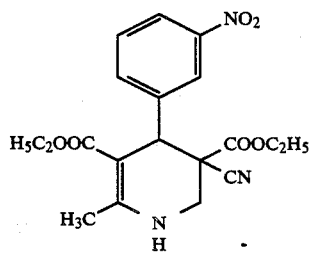

A mixture of 2.6 g (0.01 mol) of ethyl 3-nitrobenzylideneacetoacetate, 20 ml of acetic acid, 2.4 g (0.03 mol) of ammonium acetate and 1.3 g (0.01 mol) of ethyl a-cyanoacrylate is stirred at 100° C. for 10 hours. After cooling, the mixture is poured onto an ice-water mixture, the aqueous phase is separated off and the oily residue is taken up in chloroform. The organic phase is dried and concentrated. The residue is purified by column chromatography.

Yield: 0.8 g

Melting point: 132° C.

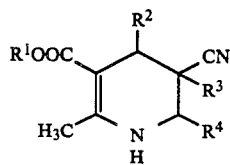

| Example No. | $R^1$ | $R^2$ | $R^3$ | $R^4$ | Melting point [°C.] |
|---|---|---|---|---|---|
| 3 | $C_2H_5$ | phenyl | $COOC_2H_5$ | 3-$NO_2$-phenyl | 174 |
| 4 | $C_2H_5$ | phenyl | CN | phenyl | 192 |
| 5 | $C_2H_5$ | phenyl | $COOC_2H_5$ | 2-$CF_3$-phenyl | 146 |
| 6 | $C_2H_5$ | 4-Cl-phenyl | $COOC_2H_5$ | 3-$NO_2$-phenyl | 219 |
| 7 | $CH_3$ | 2-$CF_3$-phenyl | $COOC_2H_5$ | H | 210 |
| 8 | $C_2H_5$ | 3-Cl-phenyl | $COOC_2H_5$ | H | 159 |
| 9 | $C_2H_5$ | 2-$NO_2$-phenyl | $COO_2H_5$ | H | 159 |
| 10 | $C_2H_5$ | 2-Cl-phenyl | $COOC_2H_5$ | H | 138 |
| 11 | $C_2H_5$ | 2-thienyl | $COOC_2H_5$ | H | 143 |

-continued

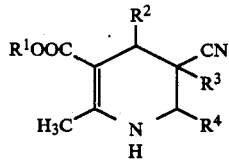

| Example No. | R¹ | R² | R³ | R⁴ | Melting point [°C.] |
|---|---|---|---|---|---|
| 12 | CH₃ | naphthyl | COOC₂H₅ | H | 121 |
| 13 | CH₃ | 3-NO₂-C₆H₄ | COOCH₂—CH(CH₃)₂ | H | 158 |
| 14 | C₂H₅ | 2,4-Cl₂-C₆H₃ | COOC₂H₅ | H | 156 |
| 15 | C₂H₅ | 3,4-Cl₂-C₆H₃ | COOC₂H₆⁵ | H | 148 |
| 16 | CH₃ | 3-NO₂-C₆H₄ | COOCH₃ | H | 142 |
| 17 | C₂H₅ | 4-Cl-C₆H₄ | COOC₂H₅ | H | 156 |
| 18 | C₂H₅ | 3-NO₂-C₆H₄ | COOCH₃ | H | 124 |
| 19 | CH₃ | 2-NO₂-C₆H₄ | COOCH₃ | H | 178 |
| 20 | C₂H₅ | 2-NO₂-C₆H₄ | COOCH₃ | H | 167 |

It is understood that the specification and examples are are illustrative but not limitative of the present invention and that other embodiments within the spirit and scope of the invention will suggest themselves to those skilled in the art.

We claim:

1. A tetrahydropyridine of the formula

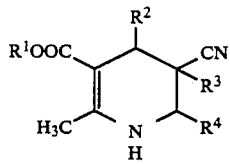

in which
- R³ represents a group of the formula —CN or —COOR⁵,
- R¹ and R⁵ each independently represents a straight-chain, branched or cyclic hydrocarbon radical which has up to 8 carbon atoms and can be interrupted in the chain by an oxygen atom and/or can be substituted by fluorine, cyano, acetoxy, hydroxyl, phenyl, phenoxy, or α-, β- or γ-pyridyl, or by an amino group, this amino group carrying two identical or different substituents from the group comprising alkyl with 1 or 2 carbon atoms and benzyl,
- R² represents phenyl, naphthyl, thienyl or pyridyl, it being possible for the ring systems mentioned to be substituted by 1 or 2 identical or different substituents from the group comprising chlorine, trifluoromethyl, nitro and cyano, and
- R⁴ represents hydrogen, or represents phenyl, which can be substituted by nitro, fluorine, chlorine or trifluoromethyl, or a pharmaceutically acceptable acid addition salt thereof.

2. A compound according to claim 1, wherein such compound is diethyl 3-cyano-6-methyl-2,4-diphenyl-1,2,3,4-tetrahydropyridine-3,5-dicarboxylate of the formula

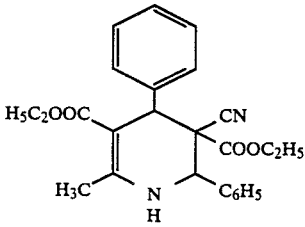

or a pharmaceutically acceptable acid addition salt thereof.

3. A compound according to claim 1, wherein such compound is diethyl 3-cyano-6-methyl-2-(3-nitrophenyl)-4-phenyl-1,2,3,4-tetrahydropyridine-3,5-dicarboxylate of the formula

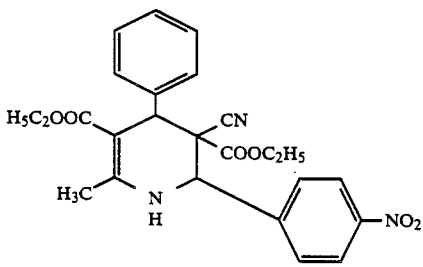

or a pharmaceutically acceptable acid addition salt thereof.

4. A compound according to claim 1, wherein such compound is 3-cyano-6-methyl-4-phenyl-3-carboethoxy-5-carbomethoxy-1,2,3,4-tetrahydropyridine of the formula

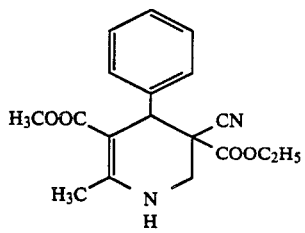

5. A compound according to claim 1, wherein such compound is diethyl 3-cyano-6-methyl-4-(thien-2-yl)-1,2,3,4-tetrahydropyridine-3,5-dicarboxylate of the formula

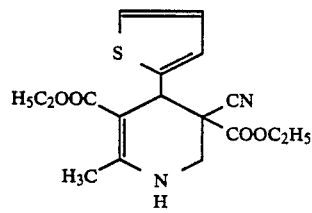

or a pharmaceutically acceptable acid addition salt thereof.

6. A compound according to claim 1, wherein such compound is 3-cyano-6-methyl-4-(3-nitrophenyl)-3-carboisobutoxy-5-carbomethoxy-1,2,3,4-tetrahydropyridine of the formula

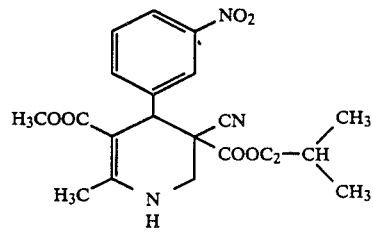

or a pharmaceutically acceptable acid addition salt thereof.

7. An anti- hypotensive or circulationrestoring composition comprising an amount effective therefor of a compound or salt according to claim 1 and a pharmaceutically acceptable diluent.

8. A unit dose of a composition according to claim 7.

9. A method of treating hypertension or a circulation disorder in a patient afflicted therewith which comprises administering to said patient in need of said treatment an effective amount of a compound or salt thereof according to claim 1.

10. The method according to claim 9, wherein such compound is
- diethyl 3-cyano-6-methyl-2,4-diphenyl-1,2,3,4-tetrahydropyridine-3,5-dicarboxylate,
- diethyl 3-cyano-3-methyl-2-(3-nitrophenyl)-4-phenyl-1,2,3,4-tetrahydropyridine-3,5-dicarboxylate,
- 3-cyano-6-methyl-4-phenyl-3-carboethoxy-5-carbomethoxy-1,2,3,4-tetrahydropyridine,
- diethyl 3-cyano-6-methyl-4-(thien-2-yl)-1,2,3,4-tetrahydropyridine-3,5-dicarboxylate or
- 3-cyano-6-methyl-4-(3-nitrophenyl)-3-carboisobutoxy-5-carbomethoxy-1,2,3,4-tetrahydropyridine, or a pharmaceutically acceptable acid addition salt thereof.

* * * * *

UNITED STATES PATENT AND TRADEMARK OFFICE
CERTIFICATE OF CORRECTION

PATENT NO. : 4,885,303                              Page 1 of 2

DATED      : December 5, 1989

INVENTOR(S) : Meyer et al.

It is certified that error appears in the above-identified patent and that said Letters Patent is hereby corrected as shown below:

Col. 11, claim 1    Delete " can be "
lines 15-16

Col. 11, claim 1    After "by" insert -- a member selected from the group
line 16             consisting of --

Col. 11, claim 1    After " substituents " insert -- selected --
line 19

Col. 11, claim 1    Delete " comprising " and substitute -- consisting of --
line 20

Col. 11, claim 1    After " substituents " insert -- selected --
lines 24-25

Col. 11, claim 1    Delete " comprising " and substitute -- consisting of --
line 25

Col. 11, claim 1    Delete 2nd " , " and substitute -- unsubstituted --
line 27

UNITED STATES PATENT AND TRADEMARK OFFICE
CERTIFICATE OF CORRECTION

PATENT NO. : 4,885,303           Page 2 of 2
DATED     : December 5, 1989
INVENTOR(S) : Meyer et al.

It is certified that error appears in the above-identified patent and that said Letters Patent is hereby corrected as shown below:

Col. 11, claim 1    Delete " which can be " and substitute -- or --
lines 27-28

Col. 11, claim 1    After " nitro " insert -- selected from group consisting
line 28             of --

Signed and Sealed this

Sixteenth Day of July, 1991

*Attest:*

HARRY F. MANBECK, JR.

*Attesting Officer*    *Commissioner of Patents and Trademarks*